(12) United States Patent
Leng et al.

(10) Patent No.: US 7,833,776 B2
(45) Date of Patent: Nov. 16, 2010

(54) **LIPIDATING SEQUENCES AND USE THEREOF FOR PRODUCING LIPIDATED PROTEINS IN *E. COLI***

(75) Inventors: Chih-Hsiang Leng, Miaoli County (TW); Hsin-Wei Chen, Miaoli County (TW); Pele Choi-Sing Chong, Miaoli County (TW); Shih-Jen Liu, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/331,576

(22) Filed: Dec. 10, 2008

(65) Prior Publication Data

US 2009/0221499 A1     Sep. 3, 2009

Related U.S. Application Data

(60) Provisional application No. 61/013,206, filed on Dec. 12, 2007.

(51) Int. Cl.
*C07H 21/04* (2006.01)
*C12N 1/20* (2006.01)

(52) U.S. Cl. ............... 435/252.33; 435/320.1; 435/69.7; 435/69.8; 435/71.1; 536/23.4; 536/23.7

(58) Field of Classification Search ............ None
See application file for complete search history.

(56) References Cited

U.S. PATENT DOCUMENTS

| 4,745,069 A | 5/1988 | Mayne et al. |
| 5,942,236 A | 8/1999 | Lobet et al. |
| 6,361,966 B1 | 3/2002 | Walker et al. |
| 6,538,118 B1 | 3/2003 | Huebner et al. |
| 6,936,263 B2 | 8/2005 | Revets et al. |
| 2005/0281835 A1* | 12/2005 | Yang ................. 424/185.1 |

FOREIGN PATENT DOCUMENTS

WO     99/57280     * 11/1999

OTHER PUBLICATIONS

Legrain et al., "Production of Lipidated Meningococcal Transferrin Binding Protein 2 in *Escherichia coli*" Protein Expression and Purification 6:570-578 (1995).
De et al., "Purification and Characterization of *Streptococcis pneumoniae* palmitoylated and pneumococcal surface adhesion A expressed in *Escherichia coli*," Vaccine: 18: 1811-1821 (2000).
Cullen et al., "Construction and Evaluation of a Plasmid Vector for the Expression of Recombinant Lipoproteins in *Escherichia coli*," Plasmid 49: 18-29 (2003).
Kamalakkannan et al., "Bacterial Lipid Modification of Proteins for Novel Protein Engineering Applications," Protein, Engineering, Design & Selection 17(10): 721-729 (2004).

* cited by examiner

*Primary Examiner*—Patricia A Duffy
(74) *Attorney, Agent, or Firm*—Occhiuti Rohlicek & Tsao LLP

(57) ABSTRACT

Production in *E. coli* of a lipidated fusion protein containing a lipidating sequence derived from Ag473 and a target polypeptide.

16 Claims, 7 Drawing Sheets

Figure 1A

| Names | Constructs | Expression |
|---|---|---|
| SPE3 | | − |
| D1E3 | | + |
| D2E3 | | + |
| D3E3 | | + |

(a)

(b)

(c)

(d)

(a)

(b)

(c)

LIPIDATING SEQUENCES AND USE THEREOF FOR PRODUCING LIPIDATED PROTEINS IN *E. COLI*

CROSS-REFERENCE TO RELATED APPLICATION

This application claims the benefit of U.S. Provisional Application 61/013,206, filed Dec. 12, 2007, the content of which is incorporated herein by reference in its entirety.

BACKGROUND OF THE INVENTION

Vaccination is considered to be the most effective and efficient approach to prevent pathogen infection. A vaccine contains a pathogen-derived antigenic material, e.g., protein, for inducing protective immune responses. In general, modified proteins, such as lipidated proteins, are more immunogenic than unmodified proteins.

Proteins in certain vaccine products have been prepared by expression in *E. coli* using recombinant technology. However, *E. coli* is generally viewed as not suitable for producing modified proteins, particularly, lipidated proteins. More specifically, *E. coli* cells lipidate poorly naturally lipidated proteins and do not produce non-naturally lipidated proteins in lipidated form.

SUMMARY OF THE INVENTION

The present invention is based on the unexpected discovery that a lipidating sequence including the signal peptide domain (SP) and Domain 1 of Ag473 (see FIG. 1A) facilitates lipidation in *E. coli* of a fusion protein that includes the lipidating sequence at its N-terminus.

Accordingly, one aspect of this invention relates to an isolated nucleic acid containing a first nucleotide sequence that encodes a lipidating sequence derived from Ag473, and optionally, a second nucleotide sequence that encodes a target polypeptide, the second nucleotide sequence being downstream of the first nucleotide sequence. In one example, the lipidating sequence includes only SP and Domain 1 of Ag473. The target polypeptide, preferably heterologous to Ag473, can be a polypeptide that is not lipidated in its native state. A "polypeptide heterologous to Ag473" is a polypeptide that is not naturally found in the same species as Ag473, or that is found in the same species but not derived from Ag473, or is derived from Ag473 and only share less than 50% sequence identity to its Ag473 counterpart.

Another aspect of this invention relates to an expression plasmid containing one of the nucleic acids described above or a host *E. coli* cell transformed with the expression plasmid.

In yet another aspect, this invention features a method of producing a fusion protein in lipidated form. The method includes two steps: (1) providing a host *E. coli* cell transformed with an expression plasmid that contains a first nucleotide sequence encoding SP, a second nucleotide sequence encoding Domain 1, and a third nucleotide sequence encoding a target polypeptide; and (2) cultivating the *E. coli* host cell to allow expression of a fusion protein including, from N-terminus to C-terminus, SP, Domain 1, and the target polypeptide. The lipidation status of the fusion protein, isolated from the *E. coli* cells, can be confirmed by conventional methods.

The fusion protein produced in this method can be mixed with a carrier, e.g., an adjuvant, to form a composition for use in induction of immune responses in a subject. The fusion protein can also be used for the manufacture of a medicament for immune modulation.

The details of one or more embodiments of the invention are set forth in the description below. Other features or advantages of the present invention will be apparent from the following drawings and detailed description of one example, and also from the appended claims.

BRIEF DESCRIPTION OF THE DRAWINGS

The drawings are first described.

FIG. 1A is a diagram showing SP and Domains 1-3 in lipoprotein Ag473 and Ag473 fragments SP, D1, D2, and D3 (upper panel), as well as dengue virus E3 antigen (bottom panel), which is not lipidated in native state.

DETAILED DESCRIPTION OF THE INVENTION

Described herein is a method of producing in *E. coli* a lipidated fusion protein including a lipidating sequence derived from Ag473 or the full-length Ag473 and a target polypeptide, the lipidating sequence or Ag473 being located at the N-terminus of the fusion protein.

Figure 1A:
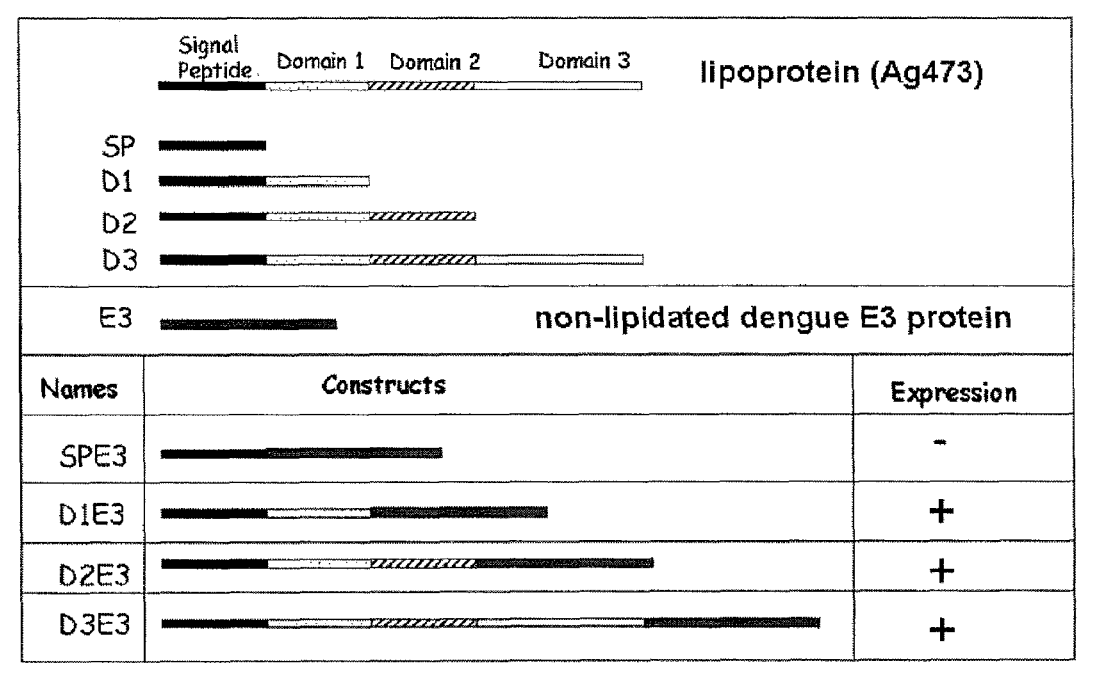
Figure 1B:
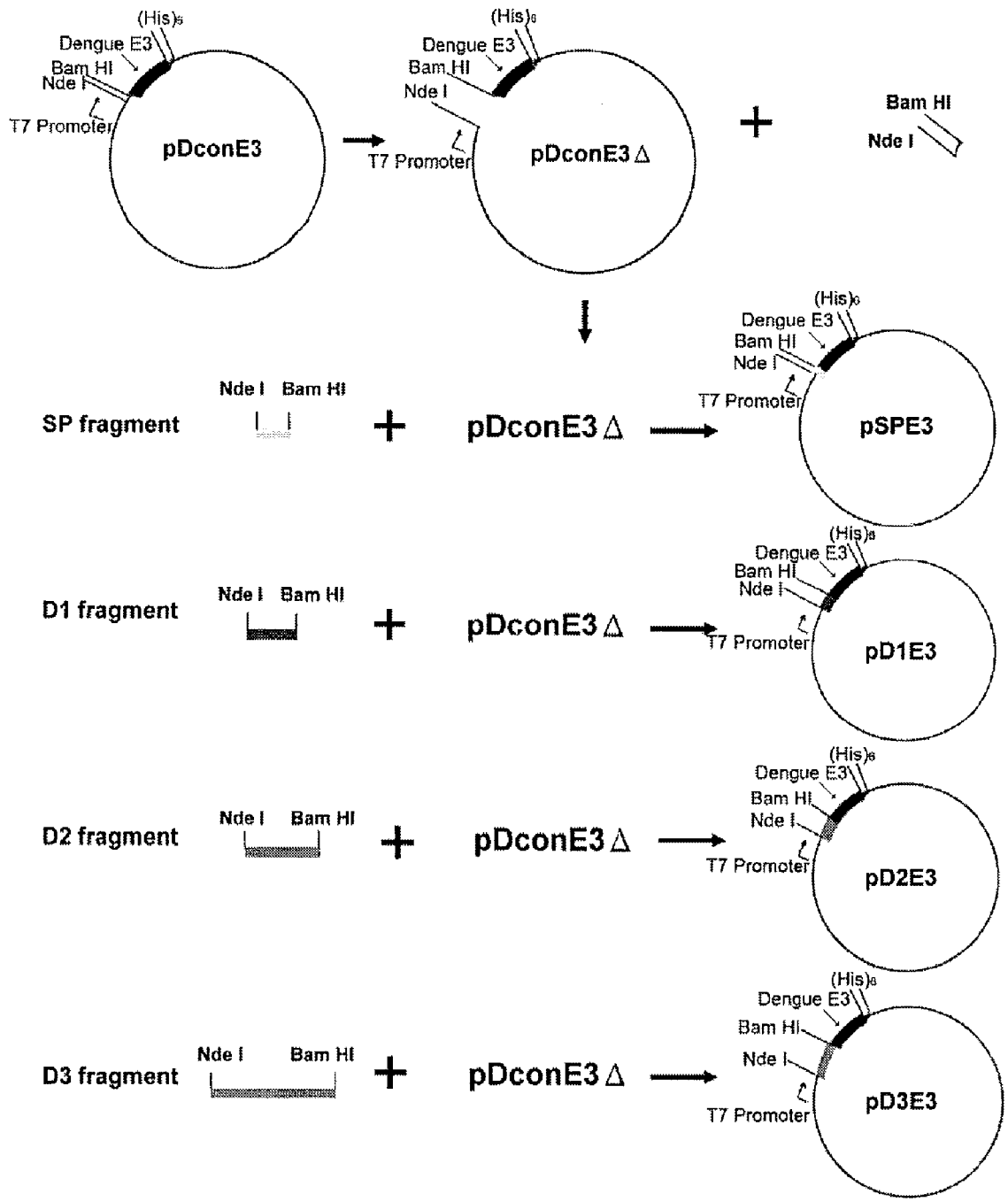
FIG. 1B is a diagram illustrating construction of expression plasmids pSPE3, pD1E3, pD2E3, and pD3E3.

Ag473 is a *Neisseria Mengitidis* lipoprotein consisting of four domains, SP and Domains 1-3. See FIG. 1A. Shown below is the amino acid sequence of this protein (SEQ ID NO: 1) with the four domains identified:

```
Met Lys Lys Leu Leu Ile Ala Ala Met Met Ala Ala Ala Leu Ala Ala Cys
1               5                   10                  15
Gln Gln Ala Lys Gln Gln Val Lys Gln Ala Val Gln Ala Val Gln Ser Asp Val
        20                  25                  30                  35
Lys Asp Thr Ala Ala Ser Ala Ala Glu Ser Ala Ala Ser Ala Val Glu Glu Ala
            40                  45                  50
Lys Asp Gln Val Lys Asp Ala Ala Ala Asp Ala Lys Ala Ser Ala Glu Glu Ala
55                  60                  65                  70
Val Thr Glu Ala Lys Glu Ala Val Thr Glu Ala Lys Glu Ala Val Thr Glu Ala
        75              80              85                      90
Lys Glu Ala Val Thr Glu Ala Ala Lys Asp Thr Leu Asn Lys Ala Ala Asp Ala
                    95              100                 105
Thr Gln Glu Ala Ala Asp Lys Met Lys Asp Ala Ala Lys
        110                 115                 120

SP: amino acid residues 1-17 in SEQ ID NO: 1 (underlined)
Domain 1: amino acid residues 18-40 in SEQ ID NO: 1 (highlited)
Domain 2: amino acid residues 41-71 in SEQ ID NO: 1 (bold face)
Domain 3: amino acid residues 72-121 in SEQ ID NO: 1 (italic)
```

The term "lipidating sequence" used herein refers to the amino acid sequence of a non-naturally occurring peptide that (a) includes a first fragment that is at least 80% (85%, 90%, 95%, or 99%) identical to SP of Ag473 and a second fragment at least 80% (85%, 90%, 95%, or 99%) identical to Domain 1 of Ag473, the first fragment being at the N-terminus of the lipidating sequence, and (b) facilitates lipidation in *E. coli* of a polypeptide carrying the lipidating sequence at its N-terminus. In the lipidating sequence, the first fragment is linked to the second fragment either directly or via a peptide linker. Preferably, this sequence has a maximum length of 40-100 (e.g., 40-80) amino acids. In one example, the lipidating sequence described herein includes SP and Domain 1.

As used herein, "percent homology" of two amino acid sequences is determined using the algorithm described in Karlin and Altschul, *Proc, Natl. Acad. Sci. USA* 87:2264-2268, 1990, modified as described in Karlin and Altschul, *Proc, Natl. Acad. Sci. USA* 90:5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

The lipidating sequence mentioned above can be linked to a target polypeptide to form a fusion protein, which is in lipidated form when expressed in *E. coli* by conventional recombinant technology. An example follows. A DNA fragment encoding the lipidating sequence and a DNA fragment encoding the target polypeptide are inserted into an expression vector, preferably carrying a strong promoter (e.g., T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured C under suitable conditions for protein expression. It is preferred that the *E. coli* host strain be resistant to the toxic effects induced by over-expression of exogenous proteins. Such *E. coli* strains can be identified/generated by the methods described in U.S. Pat. No. 6,361,966. Examples of these *E. coli* strains include, but are not limited to, C43(DE3) (ECCC B96070445), C41(DE3) (ECCC B96070444), CO214(DE3), DK8(DE3)S(NCIMB 40885), and C2014 (DE3) (NCIMB 40884).

Preferably, the fusion protein thus expressed is isolated from the *E. coli* host cells and its lipidation status is confirmed via methods known in the art, e.g., immunoblotting with an anti-lipoprotein antibody or mass spectrometry.

This lipidated fusion protein can be mixed with a pharmaceutically acceptable carrier such as a phosphate buffered saline, a bicarbonate solution, or an adjuvant to produce a pharmaceutical composition. The carrier must be "acceptable" in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. In one example, the fusion protein is mixed with an adjuvant to form a composition useful for immune modulation. This composition may be prepared as injectables, as liquid solutions or emulsions. See U.S. Pat. Nos. 4,601,903; 4,599,231; 4,599,230; and 4,596, 792. Examples of an adjuvant include, but are not limited to, cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery. See Audran R. et al. Vaccine 21:1250-5, 2003; and Denis-Mize et al. Cell Immunol., 225:12-20, 2003.

Any of the pharmaceutical compositions described above may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Described below is an example of expression and characterization of fusion proteins each including an Ag473-derived lipidating sequence and Dengue virus antigen E3.

Expression of Lipidated Peptide-E3 Fusion Proteins

The Ag473 fragments SP, D1, D2, and D3 shown in FIG. 1A were obtained by PCR using the primers listed below:

```
SP forward primer:
                                          (SEQ ID NO: 2)
5'-ATGAAAAAACTGCTGATTGCGGCGATGATGGCGGCGGCGCTGGCGGC
GTGCAGC-3';

SP reverse primer:
                                          (SEQ ID NO: 3)
5'-GCTGCACGCCGCCAGCGCCGCCGCCATCATCGCCGCAATCAGCAGTT
TTTTCAT-3';

D1 forward primer:
                                          (SEQ ID NO: 4)
5'-GGAATTCCATATGAAAAAATTATTGATTGC-3';

D1 reverse primer:
                                          (SEQ ID NO: 5)
5'-CGGGATTCCGCAGTGTCTTTAACATCGGA-3';

D2 forward primer:
                                          (SEQ ID NO: 4)
5'-GGAATTCCATATGAAAAAATTATTGATTGC-3';

D2 reverse primer:
                                          (SEQ ID NO: 6)
5'-CGGGATTCTTCCTCGGCACTTGCCTT-3';

D3 forward primer:
                                          (SEQ ID NO: 4)
5'-GGAATTCCATATGAAAAAATTATTGATTGC-3';

D3 reverse primer:
                                          (SEQ ID NO: 7)
5'-CGGGATTCTTTGGCGGCATCTTTCATTTTGTC-3'.
```

The PCR products thus obtained were cloned into plasmid pDconE3 to produce expression plasmids pSPE3, pD1E3, pD2E3, and pD3E3, which encode fusion proteins containing (1) dengue virus E3 antigen and (2) SP (SEQ ID NO: 8), D1

(SEQ ID NO: 9), D2 (SEQ ID NO: 10), and D3 (SR) ID NO: 1), respectively. See FIG. 1B. pDconE3 contains a nucleotide sequence encoding the dengue virus E3 antigen fused with a hexahistidine tag at its C-terminus.

The expression plasmids noted above were introduced into *E. coli* strain C43(DE3) (Imaxio, Saint-Beauzire, France) via conventional recombinant technology and positive transformants were selected. The transformants were cultured at 37° C. overnight and then induced with 1 mM of IPTG for 3 h. The *E. coli* cells were harvested afterwards by centrifugation and lyzed. The cell lysates were first analyzed by SDS-PAGE to determine presence of the fusion proteins, i.e., SPE3, D1E3, D2E3, and D3E3, expressed from these expression plasmids.

Results thus obtained showed that fusion protein SPE3 was expressed in C43(DE3) at a very low level, In contrast, the expression levels of fusion proteins D1E3, D3E3, and D3E3 were significantly higher. See FIG. 2, panel (b).

The expression of fusion proteins SPE3, D1E3, D2E3, and D3E3 were further confirmed by immunoblotting. Briefly, the proteins separated on the SDS-gel mentioned above were transferred to a polyvinylidene difluoride (PVDF) membrane (Millipore, Billerica, Mass., USA) at 400 mA for 25 min. The membrane was blocked overnight at 4° C. in PBST (PBS containing 0.05% Tween-20) in the presence of 5% non-fat milk. After being washed with PBST, the membrane was incubated at room temperature for 1 h with mouse anti-His antibodies (1:1500 dilution, Amersham Biosciences, New Territories, HK), washed with PBST again, and then incubated with horseradish peroxidase (HRP)-conjugated goat anti-mouse IgG (1:5000, Bethyl Laboratories, Montgomery, Tex., USA) for 1 h. Then, the membrane incubated with 0.2 mM DAB (3,3'-diaminobenzidine tetrahydrochloride, Sigma, St. Louis, Mo., USA) for 2-3 min to develop the signal released from HRP. Results obtained from this immunoblotting analysis also show that D1E3, D2E3, and D3E3 expressed at high levels in C43(DE3).

The N-terminal amino acid sequences of the fusion proteins D11E3, D2E3, and D3E3 could not be determined by Edman degradation, indicating that their N-terminal were blocked.

Characterization of Fusion Protein D1E3

Recombinant E3 (rE3), expressed from pDconE3, and fusion protein D1E3, expressed from pD1E3, were isolated from C43(DE3) cells by immobilized metal affinity chromatography (IMAC) as follows. *E. coli* cells were harvested from 2.4 liter cell cultures by centrifugation (8000×g for 20 min) and the pellets thus collected were re-suspended in 100 ml of a homogenization buffer containing 20 mM Tris-Cl (pH 8.0), 500 mM NaCl, 10% glycerol, 50 mM sucrose, and 10 mM imidazole). The *E. coli* cells were then disrupted using a French Press (Constant Systems, Daventry, UK) at 27 Kpsi in the presence of a detergent and the cell lysates thus obtained were centrifuged at 80,000×g for 60 min. The supernatants were collected and loaded onto a column (2.2 cm i.d.×5.3 cm) filled with 20 ml Ni-NTA resin (Qiagen, San Diego, Calif., USA). The column was washed first with the homogenization buffer and then with the same buffer containing 50 mM imidazole. The recombinant proteins were eluted with the homogenization buffer containing 500 mM imidazole and characterized by both SDS-PAGE and immunoblotting. Results thus obtained indicate that both rE3 and D1E3 were isolated with high purity.

Fusion protein D1E3 was then subjected to mass spectrometry (MS) analysis as described below. The protein was first dialyzed against 5 mM ammonium bicarbonate at pH 8.5 and then treated with trypsin (Promega Co., Madison, Wis.) at a D1E3: trypsin ratio of 50:1 (Wt/Wt) in 25 mM ammonium bicarbonate (pH 8.5) for 2 hours at room temperature. The enzymatic reaction was terminated by addition of formic acid (final concentration 1.2%). One µl of the typsin-digested protein was mixed with 1 µl of a saturated solution of α-ciano-4-hydrozycinnamic acid (Sigma) in acetonitrile/0.1% trifluoroacetic acid (1:3, vol/vol). One microliter of the mixture was placed on the target plate of a matrix-assisted laser desorption ionization time-of-flight (MALDI-TOF) mass spectrometer (Burker) for analysis. The MS peaks obtained from this analysis represent the peptides obtained from complete trypsin-digestion of D1E3. These peptides correspond to the C-terminal fragments of the fusion protein. The MS results also indicate that these peptides are not modified.

The fusion protein was then subjected to partial trypsin digestion (10 minutes digestion). Results obtained from MALDI-TOF analysis as described above indicate that the partial trypsin digestion products correspond to the N-terminal fragments of D1E3 and these peptides are lipidated.

Take together, it is demonstrated that fusion protein D1E3 is a lipoprotein.

Bioactivity of Lipoprotein D1E3

The ability of D1 E3 to activate bone marrow-derived dendritic cells (BM-DC) was examined as follows. Mouse BM-DCs were isolated and cultured in vitro following the methods described in Lutz et. al. 1999, J Immunol Methods 223:77-92. Briefly, femurs and tibiae of female BALB/c mice at the age of 6-8 weeks were removed and bone marrow cells contained therein were separated by vigorous pipetting. After removing red blood cells with a lysis buffer, the remaining bone marrow cells were suspended (2-5×10$^5$/mL) in Roswell Park Memorial Institute (RPMI) medium-10: RPMI-1640 (GIBCO BRL, Grand Island, N.Y.) supplemented with penicillin (100 U/mL, Sigma, St Louis, Mo.), streptomycin (100 g/mL, Sigma), L-glutamine (2 mM, Sigma), 2-mercaptoethanol (50 M, Sigma), and 10% heat-inactivated FBS. On days 0, 3, 6, and 8, bone marrow cells were transferred to a fresh RPMI-10 medium containing 200 U/mL (20 ng/mL) of recombinant granulocyte macrophage colony stimulating factor (MoGM-CSF, Peprotech, Rocky Hill, N.J., USA) and cultured in Petri dishes.

Nine days later, the cells (5-10×10$^5$) were stained with 50 µL of fluorescence-conjugated antibodies specific to DC surface markers, i.e., MHC class II molecules including I-Ad/I-Ed, CD80 (B7-1), CD86 (B7-2), or CD11c, or isotype-matched control antibodies (BD Pharmingen, San Diego, Calif., USA). All of the antibodies were dissolved in PBS containing 1% bovine serum albumin (BSA) and 0.1% azide. The stained cells were analyzed by Fluorescence-activated cell sorting (FACS) analysis using FASCalibur flow cytometer (BD Bioscience, San Diego, Calif., USA). The results indicate that 50% of the total cultured cells are immature dendritic cells.

Figure 2:
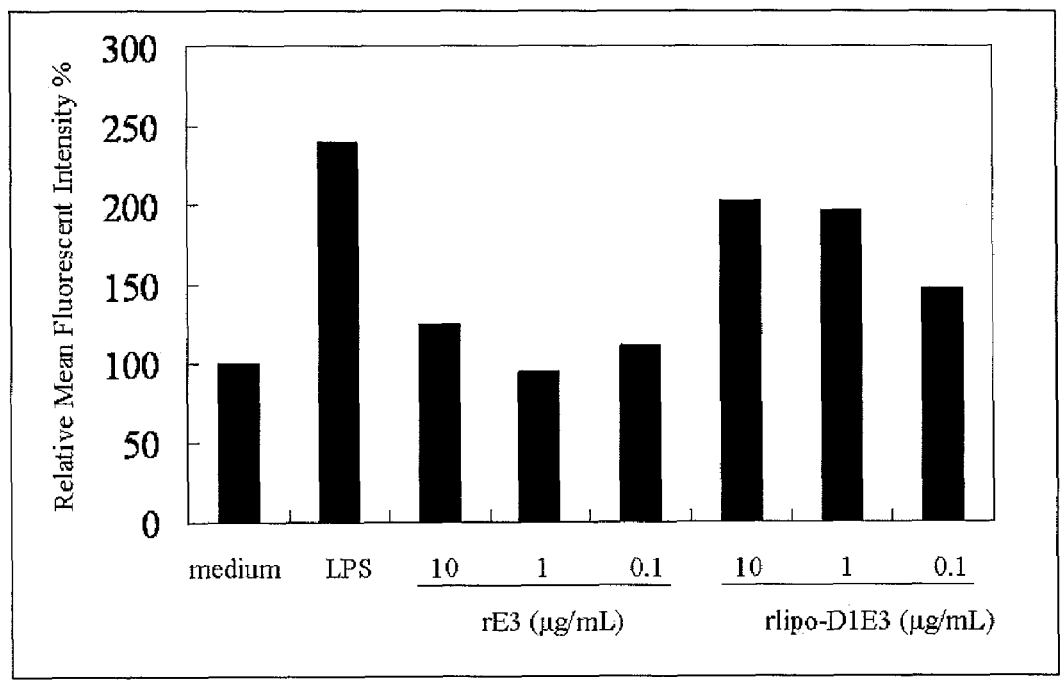
FIG. 2 is a number of charts showing the levels of certain surface markers of dendritic cells treated with lipopolysacharamide (LPS, a positive control), recombinant E3 (rE3), or fusion protein D1E3. (a): MHC Class II; (b): CD40; (c): CD80; and (d): CD86.
Figure 2:
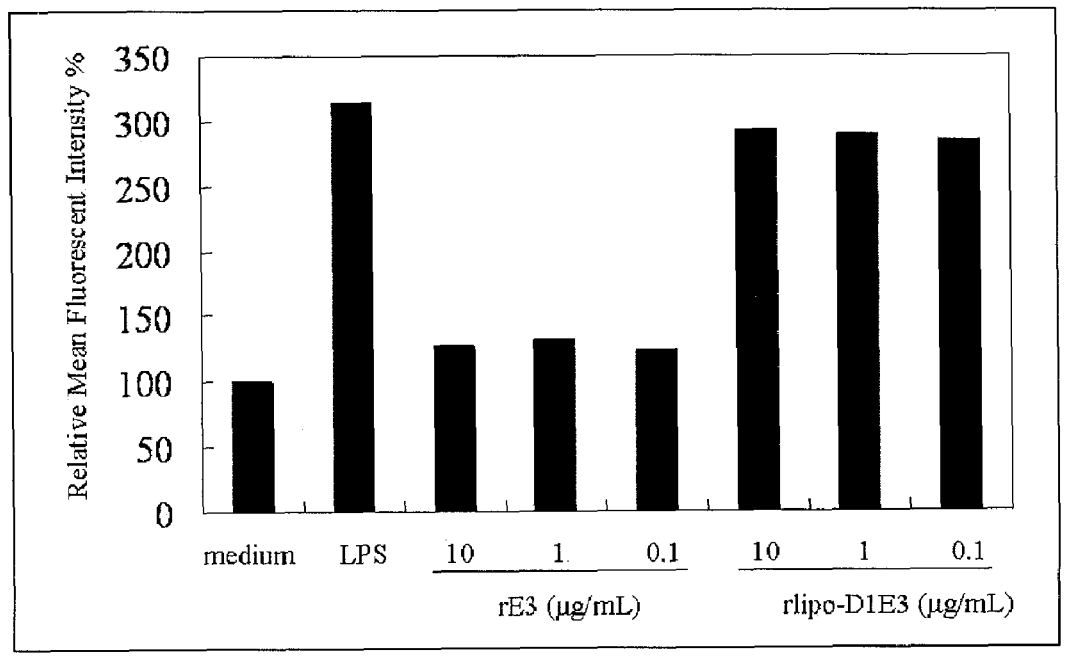
Figure 2:
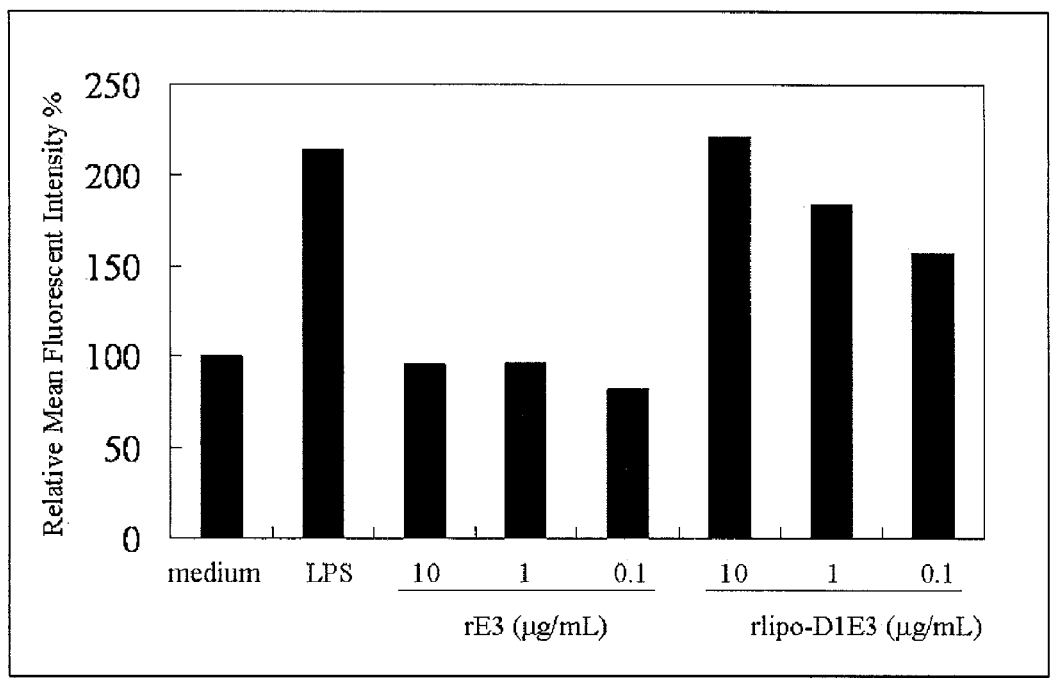
Figure 2:
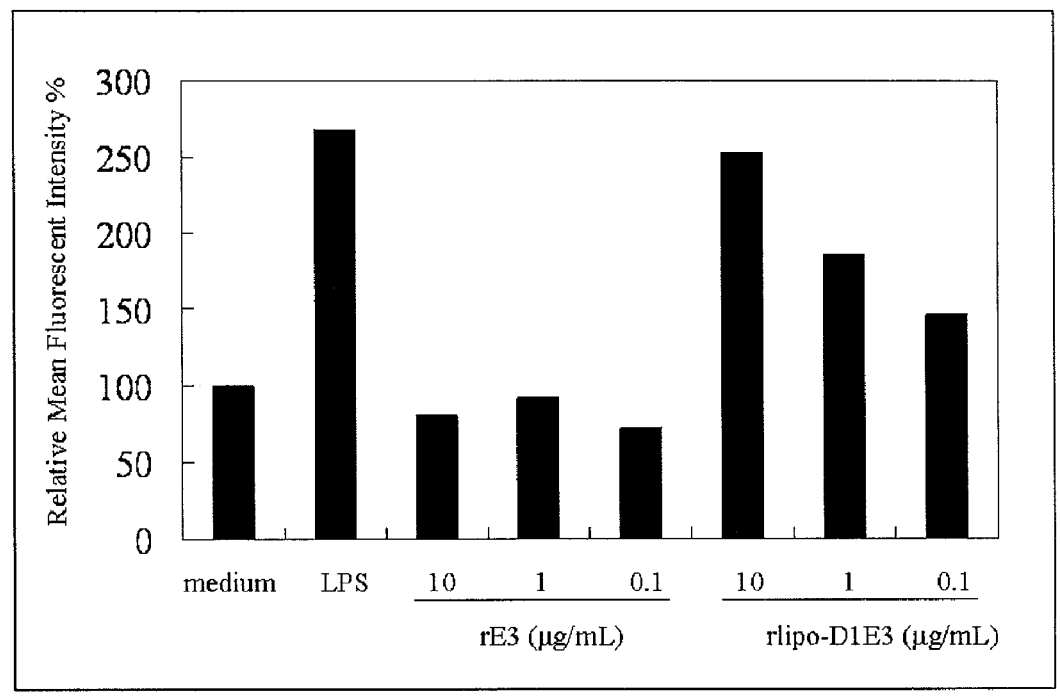

The cultured cells were incubated with rE3, D1E3, or LPS at various concentrations (10 µg/ml, 1 µg/ml, or 0.1 µg/ml) for 6 days. They were then examined for the levels of DC surface markers, i.e., MHC Class II, CD40, CD80, and CD86, following the method described above. As shown in FIG. 2, D1E3 increased the levels of these DC surface markers in a dose-dependent manner, indicating that this fusion protein activated DC cells. In contrast, the levels of these markers were not increased in the cells treated with rE3.

Figure 3:
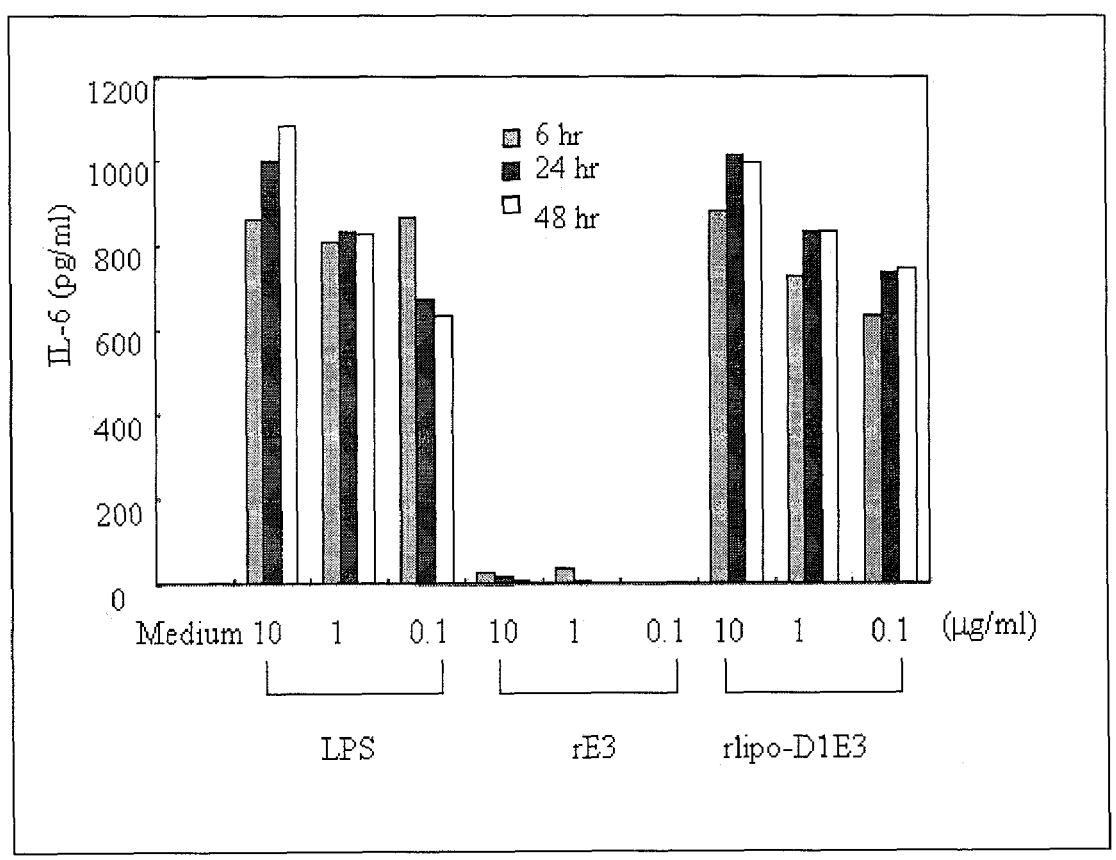
FIG. 3 is a number of charts showing levels of cytokine secretion of dendritic cells treated with LPS, rE3, or D1E3. (a): IL-6; (b): IL-12; and (c): TNF-alpha.
Figure 3:
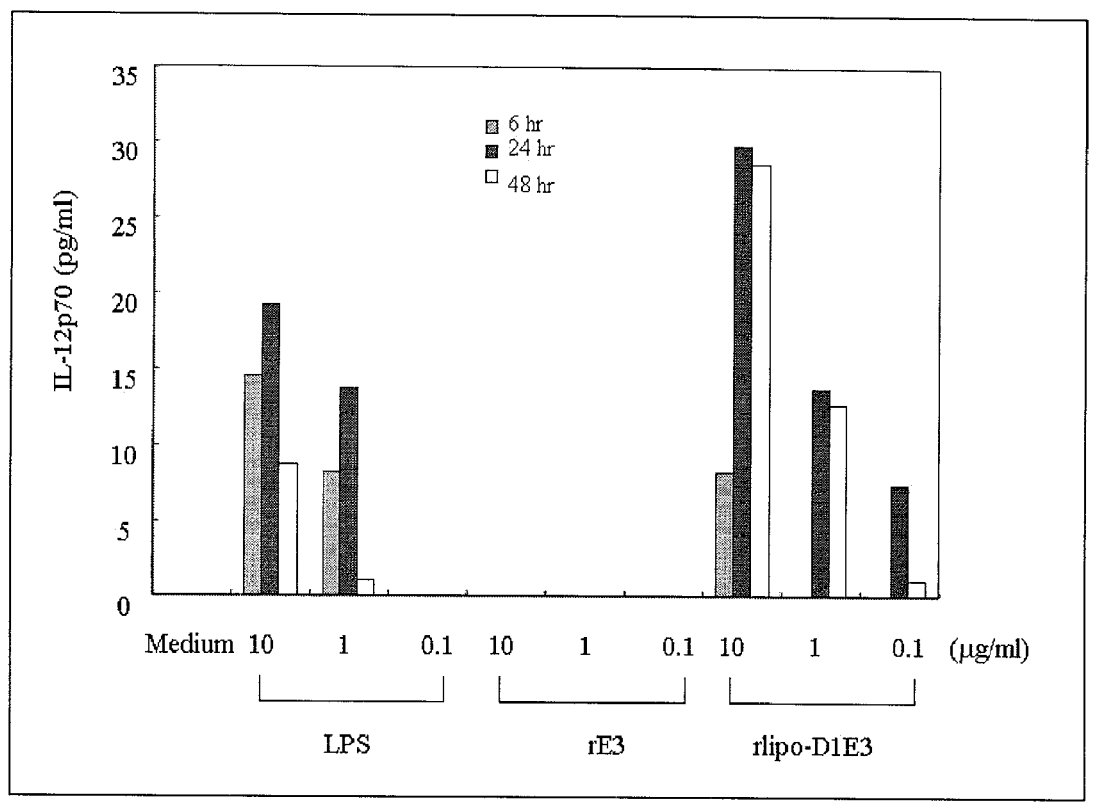
Figure 3:
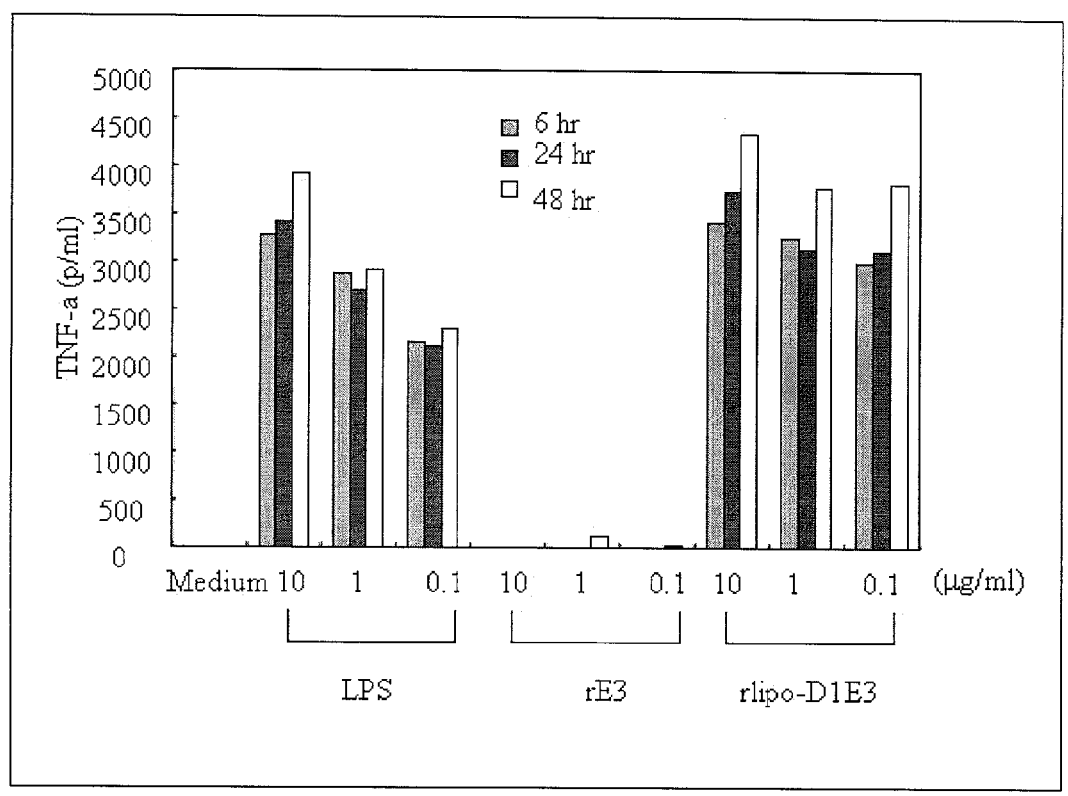

The treated BM-DC cells were further examined for secretion of cytokines, including IL-6, TNF-alpha, and IL-12 by ELISA (eBioscience, San Diego, Calif.). As shown in FIG. 3, D1E3, not rE3, induced cytokine secretion in BM-DC cells, indicating that this lipidated protein is highly immunogenic than its non-lipidated counterpart.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated nucleic acid, comprising
a first nucleotide sequence encoding a lipidating sequence that includes residues 1-17 in SEQ ID NO:1 and residues 18-40 in SEQ ID NO:1, the residues 1-17 in SEQ ID NO:1 being located at the N-terminus of the lipidating sequence, and
a second nucleotide sequence encoding a target polypeptide, which is heterologous to the lipidating sequence;
wherein the second nucleotide sequence is located downstream of the first nucleotide sequence.

2. The nucleic acid of claim 1, wherein the lipidating sequence consists of residues 1-40 in SEQ ID NO:1.

3. The nucleic acid of claim 1, wherein the target polypeptide is not lipidated in native state.

4. The nucleic acid of claim 1, wherein the nucleic acid is an expression plasmid.

5. The nucleic acid of claim 4, wherein the target polypeptide is not lipidated in native state.

6. A host *E. coli* cell, comprising the nucleic acid of claim 4.

7. The host cell of claim 6, wherein the target polypeptide is not lipidated in native state.

8. A method for producing a recombinant lipidated fusion protein, said method comprising
providing an *E. coli* host cell transformed with an expression plasmid, including a first nucleotide sequence that encodes residues 1-17 in SEQ ID NO:1, a second nucleotide sequence that encodes residues 18-40 in SEQ ID NO:1, and a third nucleotide sequence that encodes a target polypeptide, wherein the expression plasmid encodes a fusion protein containing, from N-terminus to C-terminus, residues 1-17 in SEQ ID NO:1, residues 18-40 in SEQ ID NO:1, and the target polypeptide, and
cultivating the *E. coli* host cell to allow expression of the fusion protein in lipidated form.

9. The method of claim 8, wherein in the fusion protein, residues 1-17 in SEQ ID NO:1 links directly to residues 18-40 in SEQ ID NO:1.

10. The method of claim 9, wherein the target polypeptide is not lipidated in native state.

11. The method of claim 8, further comprising, after the cultivation step, isolating the fusion protein thus expressed and confirming that the fusion protein is lipidated.

12. The method of claim 11, wherein, in the fusion protein, residues 1-17 in SEQ ID NO:1 links directly to residues 18-40 in SEQ ID NO:1.

13. The method of claim 12, wherein the target polypeptide is not lipidated in native state.

14. The nucleic acid of claim 1, wherein the lipidating sequence has a maximum length of 100 amino acids.

15. The nucleic acid of claim 4, wherein the lipidating sequence has a maximum length of 100 amino acids.

16. The host cell of claim 6, wherein the lipidating sequence has a maximum length of 100 amino acids.

* * * * *

SEQUENCE LISTING

```
<160> NUMBER OF SEQ ID NOS: 10

<210> SEQ ID NO 1
<211> LENGTH: 121
<212> TYPE: PRT
<213> ORGANISM: Neisseria meningitidis

<400> SEQUENCE: 1

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
    50                  55                  60

Ala Lys Ala Ser Ala Glu Glu Ala Val Thr Glu Ala Lys Glu Ala Val
65                  70                  75                  80

Thr Glu Ala Lys Glu Ala Val Thr Glu Ala Lys Glu Ala Val Thr Glu
                85                  90                  95

Ala Ala Lys Asp Thr Leu Asn Lys Ala Ala Asp Ala Thr Gln Glu Ala
            100                 105                 110

Ala Asp Lys Met Lys Asp Ala Ala Lys
        115                 120

<210> SEQ ID NO 2
<211> LENGTH: 54
<212> TYPE: DNA
<213> ORGANISM: Artificial Sequence
<220> FEATURE:
<223> OTHER INFORMATION: Forward Primer

<400> SEQUENCE: 2
atgaaaaaac tgctgattgc ggcgatgatg gcggcggcgc tggcggcgtg cagc          54

<210> SEQ ID NO 3
<211> LENGTH: 54
<212> TYPE: DNA
<213> ORGANISM: Artificial Sequence
<220> FEATURE:
<223> OTHER INFORMATION: Reverse Primer

<400> SEQUENCE: 3
gctgcacgcc gccagcgccg ccgccatcat cgccgcaatc agcagttttt tcat          54

<210> SEQ ID NO 4
<211> LENGTH: 30
<212> TYPE: DNA
<213> ORGANISM: Artificial Sequence
<220> FEATURE:
<223> OTHER INFORMATION: Forward Primer
```

<400> SEQUENCE: 4
ggaattccat atgaaaaaat tattgattgc                                    30

<210> SEQ ID NO 5
<211> LENGTH: 29
<212> TYPE: DNA
<213> ORGANISM: Artificial Sequence
<220> FEATURE:
<223> OTHER INFORMATION: Reverse Primer

<400> SEQUENCE: 5
cgggattccg cagtgtcttt aacatcgga                                     29

<210> SEQ ID NO 6
<211> LENGTH: 26
<212> TYPE: DNA
<213> ORGANISM: Artificial Sequence
<220> FEATURE:
<223> OTHER INFORMATION: Reverse Primer

<400> SEQUENCE: 6
cgggattctt cctcggcact tgcctt                                        26

<210> SEQ ID NO 7
<211> LENGTH: 32
<212> TYPE: DNA
<213> ORGANISM: Artificial Sequence
<220> FEATURE:
<223> OTHER INFORMATION: Reverse Primer

<400> SEQUENCE: 7
cgggattctt tggcggcatc tttcattttg tc                                 32

<210> SEQ ID NO 8
<211> LENGTH: 17
<212> TYPE: PRT
<213> ORGANISM: Neisseria meningitides

<400> SEQUENCE: 8

Met Lys Lys Leu Leu Ile Ala Ala Met Met Ala Ala Ala Leu Ala Ala
 1               5                  10                  15

Cys

<210> SEQ ID NO 9
<211> LENGTH: 40
<212> TYPE: PRT
<213> ORGANISM: Neisseria meningitidis

<400> SEQUENCE: 9

Met Lys Lys Leu Leu Ile Ala Ala Met Met Ala Ala Ala Leu Ala Ala
 1               5                  10                  15

Cys Ser Gln Glu Ala Lys Gln Glu Val Lys Glu Ala Val Gln Ala Val
                 20                  25                  30

Glu Ser Asp Val Lys Asp Thr Ala
         35                  40

<210> SEQ ID NO 10
<211> LENGTH: 71
<212> TYPE: PRT
<213> ORGANISM: Neisseria meningitidis

<400> SEQUENCE: 10

-continued

```
Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
    50                  55                  60

Ala Lys Ala Ser Ala Glu Glu
65                  70
```